(12) United States Patent
Hughes

(10) Patent No.: US 8,030,040 B2
(45) Date of Patent: *Oct. 4, 2011

(54) PRODUCTION OF A FERMENTATION PRODUCT

(75) Inventor: Jonathan Hughes, West Yorkshire (GB)

(73) Assignee: Ciba Specialty Chemicals Water Treatments Ltd., West Yorkshire, Bradford (GB)

( * ) Notice: Subject to any disclaimer, the term of this patent is extended or adjusted under 35 U.S.C. 154(b) by 649 days.

This patent is subject to a terminal disclaimer.

(21) Appl. No.: 10/523,230

(22) PCT Filed: Jul. 28, 2003

(86) PCT No.: PCT/EP03/08295

§ 371 (c)(1),
(2), (4) Date: Jan. 31, 2005

(87) PCT Pub. No.: WO2004/015146

PCT Pub. Date: Feb. 19, 2004

(65) Prior Publication Data

US 2005/0272134 A1     Dec. 8, 2005

(30) Foreign Application Priority Data

Aug. 5, 2002 (GB) .................................. 0218012.3

(51) Int. Cl.
```
C12P 7/10      (2006.01)
C12P 7/20      (2006.01)
C12P 7/16      (2006.01)
C12P 7/08      (2006.01)
C12P 9/00      (2006.01)
C13K 1/02      (2006.01)
```
(52) U.S. Cl. ........ 435/165; 435/159; 435/160; 435/163; 435/161; 435/131; 127/37

(58) Field of Classification Search .................. 435/161, 435/165

See application file for complete search history.

(56) References Cited

U.S. PATENT DOCUMENTS 4,384,897 A * 5/1983 Brink .............................. 127/37

(Continued)

FOREIGN PATENT DOCUMENTS

EP          0102759          3/1984

(Continued)

OTHER PUBLICATIONS

Dissociation Constants of Inorganic Acids and Bases, CRC Handbook of Chemistry and Physics, 2006-2007, CRC Press, 87th edition, 8-40-8-41.*

(Continued)

*Primary Examiner* — Sue Liu
*Assistant Examiner* — Sheridan MacAuley
(74) *Attorney, Agent, or Firm* — Shruti S. Costales

(57) ABSTRACT

A process of producing fermentation product comprising, forming an acidified suspension of particulate plant derived material comprising a first polysaccharide which is more readily hydrolysable and a second polysaccharide which is more difficult to hydrolyse; allowing the first polysaccharide to undergo hydrolysis under conditions such that the first polysaccharide is hydrolysed, thereby forming a mixture of an aqueous liquor containing dissolved sugar and a solid residue containing the second polysaccharide; subjecting the acidic mixture to one or more separation stages in which the solid residue and aqueous sugar liquor are substantially separated from each other; passing the aqueous liquor to a fermentation stage where the dissolved sugars are acted upon by a microorganism in a broth to produce a fermentation product; and separating the fermentation product from the broth, characterised in that the separation stage uses one or more flocculating agent(s) to form a waste by-product.

14 Claims, 4 Drawing Sheets

U.S. PATENT DOCUMENTS

| | | | |
|---|---|---|---|
| 4,612,286 A | 9/1986 | Sherman et al. | 435/157 |
| 5,366,558 A | 11/1994 | Brink | 127/43 |
| 5,411,594 A * | 5/1995 | Brelsford | 127/37 |
| 5,529,699 A * | 6/1996 | Kuo et al. | 210/735 |
| 7,582,444 B2 * | 9/2009 | Hughes | 435/41 |

FOREIGN PATENT DOCUMENTS

| | | | |
|---|---|---|---|
| EP | 0150933 | | 8/1985 |
| EP | 0202780 | | 11/1986 |
| EP | 0964061 | | 12/1999 |
| GB | 376372 | * | 1/1931 |
| GB | 2017707 | * | 10/1979 |
| JP | 61204100 | | 9/1986 |
| WO | WO 94/29475 | * | 12/1994 |
| WO | WO 99/50195 | * | 10/1999 |
| WO | WO 01/34908 | * | 5/2001 |

OTHER PUBLICATIONS

Kholkin et al., 1999, Applied Biochemistry and Biotechnology, 82, 135-140.*

Derwent Abstr. 1993-150324 for SU 1733477 (1992).

Derwent Abstr. 1997-488205 for RU 2077594 (1997).

Derwent Abstr. 1986-281090 [43] for JP 61204100 (1986).

K. Kim et al., Applied Biochemistry and Biotechnology, vol. 91-93, (2001), pp. 253-267.

* cited by examiner

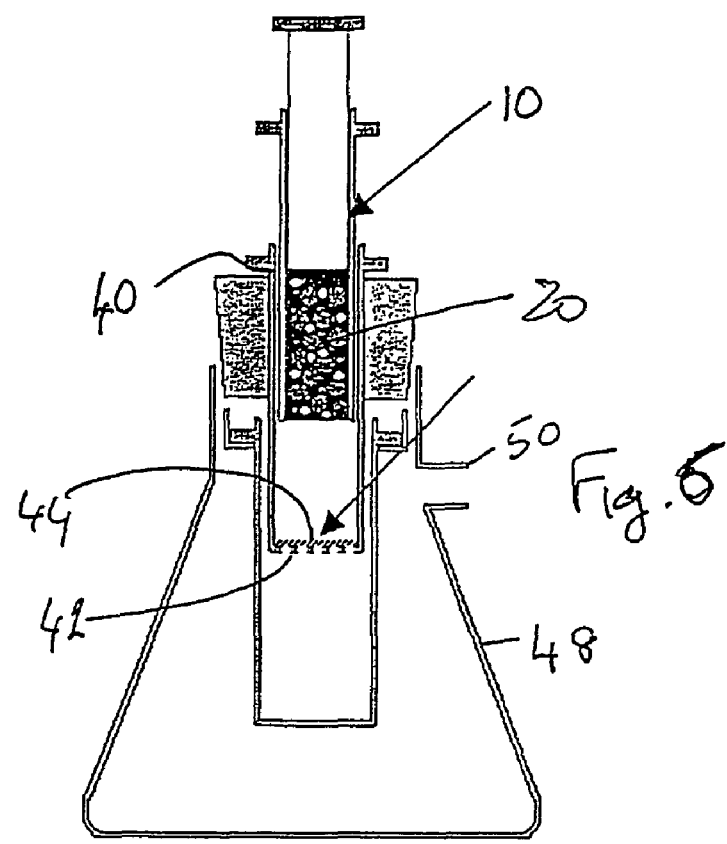
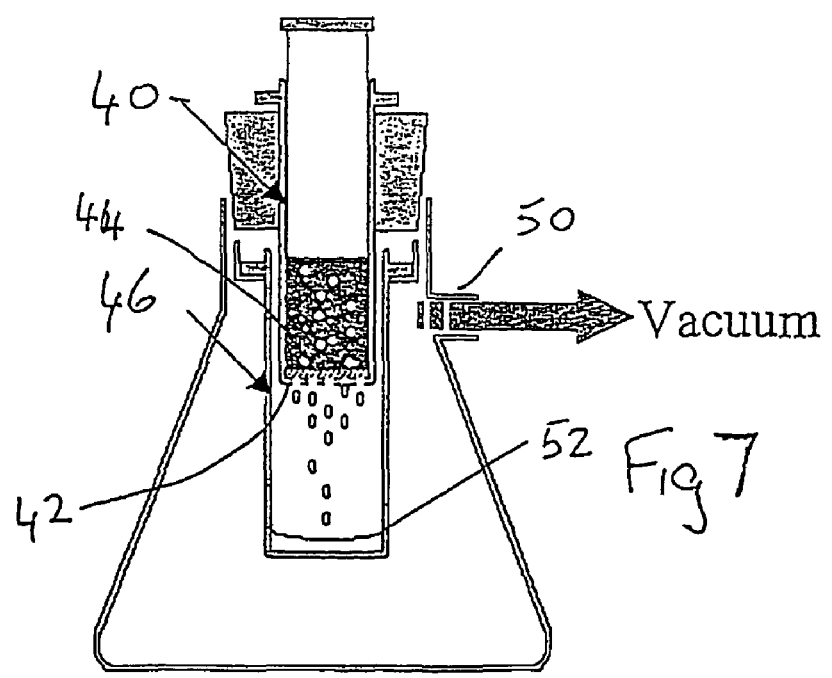

PRODUCTION OF A FERMENTATION PRODUCT

The present invention relates to processes of treating plant derived material to provide an aqueous liquor containing sugars which are used in a fermentation process to produce a fermentation product. Typically such fermentation products include for instance ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxy propionic acid, glyconic acid, tartaric acid and amino acids such as L-glutaric acid, L-lysine, L-aspartic acid, L-tryptophan, L-arylglycines or salts of any of these acids.

It is known to treat a biomass with acid in order to hydrolyse polysaccharides to the component sugars that can be used in a fermentation process to produce a fermentation product. For instance U.S. Pat. No. 4,384,897 describes a method of treating biomass material in which it is subjected to a two stage hydrolysis in which polysaccharides that are more easily hydrolysed, such as hemicellulose and then in a second stage the material that is more difficult to depolymerise e.g. cellulose, is degraded using a more severe hydrolytic treatment. The products of the first and second stages include sugar solutions, organic acids and aldehydes. The monosaccharides produced are subjected to a fermentation step to generate ethanol and the beer resulting from the fermentation may then be subjected to rectification to produce ethanol of commercial grade. U.S. Pat. No. 4,384,897 sets out to provide improvements for the more efficient washing of solids, the use of co-current washing or countercurrent washing of solids and proposes the use of ferric and/or aluminium ions as flocculating agents to separate finely dispersed solids resulting from neutralisation of the hydrolysate liquor stream.

Kyoung Heon Kim et al (Applied Biochemistry and Biotechnology, Vol 91-93, pg 253-267) investigates the continuous countercurrent hydrolysis and extraction of hemicellulose from wood residues pre-treated with acid and considers the effect on drainage rate of such a pre-treated biomass. A continuous countercurrent screw extractor used relies on the percolation of water by gravity through the pre-treated biomass. One difficulty identified with this process is that the pre-treated biomass has poor water drainage properties and channelling or blockage may occur inside the extractor, which can result in low sugar recovery yields or low throughput.

It would be desirable to improve the drainage rate of acid treated plant derived material in order to maximise the soluble sugars recovered in the liquor.

According to the present invention we provide a process of producing fermentation product comprising the steps of, (i) forming an acidified suspension of particulate plant derived material comprising a first polysaccharide which is more readily hydrolysable and a second polysaccharide which is more difficult to hydrolyse,
(ii) allowing the first polysaccharide to undergo hydrolysis by action of the acid at a temperature of at least 50° C. under conditions such that the first polysaccharide is hydrolysed and thereby forming a mixture of an aqueous liquor containing dissolved sugar and a solid residue containing the second polysaccharide,
(iii) subjecting the mixture to one or more separation stages in which the solid residue and aqueous sugar liquor are substantially separated from each other,
(iv) optionally washing the residue substantially free of the acid and the sugar,
(v) passing the solid cellulosic residue to a further treatment stage in which the residue is subjected to the action of dilute acid at a temperature of at least 50° C. under conditions such that the second polysaccharide is hydrolysed and thereby forming a mixture of an aqueous liquor containing dissolved sugar and a solid residue,
(vi) subjecting the mixture to one or more separation stages in which the solid residue and aqueous sugar liquor are substantially separated from each other,
(vii) optionally washing the residue substantially free of the acid and the sugar,
(viii) adjusting the pH of the aqueous liquor from stages (iii), (iv), (vi) and (vii) to a pH of at least 4,
(ix) passing the aqueous liquor from stage (viii) to a fermentation stage in order to produce a fermentation product,
(x) separating the fermentation product from the broth,
characterised in that the separation stage in steps (iii) and/or (vi) is assisted by flocculation of the by-product, employing one or more flocculating agent(s) selected from the group consisting of water soluble polymers, water swellable polymers and charged microparticulate material.

We have found that surprisingly by using the special flocculation process in the separation stage, a consistently high yield of fermentation product can be achieved. It is thought that small quantities of $C_5$ sugar resulting from the first stage remains with the harder to hydrolyse material such as cellulose. Thus it would seem likely that the more severe hydrolysis conditions of the second stage hydrolysis results in these trace amounts of sugars to be converted into furfural and possibly other aldehydes. It is believed that even trace amounts of furfural and other aldehydes tend to poison the microorganisms or enzymic biocatalysts used in the fermentation process and thus resulting in poor yields of fermentation product.

The improved separation stage in the process also has the advantage that the sugar solution resulting from the first and second stages is substantially free from extraneous solid material, such as cellulosic fibres.

The plant derived material is typically any readily available source of polysaccharides, particularly cellulosic materials. Typically the cellulosic material comprises materials selected from the group consisting of herbaceous biomass, softwood biomass, hardwood biomass, sewage sludge, paper mill sludge and the biomass fraction of municipal solid waste. The herbaceous biomass may for instance be bagasse, rice straw, rice hulls, corn stover, wheat straw, grass, trees and cotton gin trash.

Preferably the plant derived material is cellulosic and comprises hemicellulose as the first polysaccharide and cellulose as the second polysaccharide. Generally the plant derived material also contains lignin or lignin type materials, which remain in the solid by-product.

The acidified suspension may be formed by combining a particulate material comprising cellulose, hemicellulose and lignin with a dilute acid. Alternatively the suspension can be made by treatment of a cellulosic biomass with sulphur dioxide gas, steam and water at an elevated temperature. Typically the process can be conducted by impregnation of the biomass material with $SO_2$ gas followed by steam at 205 to 215° C. for 5 minutes and then the addition of water to form a slurry (Stenberg et al., 1998).

By dilute we mean that the acid generally has a concentration of less than 10% by weight. Usually though the concentration will be much lower, for instance at less than 5%. The acid may be a strong mineral acid such as hydrochloric acid, sulphuric acid, sulphurous acid, hydrofluoric acid, nitric acid or phosphoric acid. Suitable organic acids may be carbonic acid, tartaric acid, citric acid, glucuronic acid, gluconic acid, formic acid, trichloroacetic acid or similar mono- or polycarboxylic acids.

Preferably the acid is a mixture of a strong mineral acid and an organic acid. Typically the mineral acid would be at a concentration of up to 2%, preferably in the range 0.2% to 1.0%, especially around 0.7%. The organic acid may be present at a higher concentration, for instance up to 5%, especially if the acid is a relatively weak acid such as acetic acid. Preferably the organic acid would be present at a concentration between 1% and 3%, more preferably around 2%.

Ideally the acid exhibits a pKa below 4. Preferred results are obtained by using either hydrochloric acid or sulphuric acid.

The hydrolysis of the first polysaccharide is preferably carried out at a temperature of between 120 and 220° C. for a period of 1 to 15 minutes, although lower temperatures are possible if the treatment is longer. The hydrolysis of the second polysaccharide can be achieved at a temperature of between 120 and 220° C. for a period of 1 to 15 minutes. Usually the second hydrolysis step is carried out at a higher temperature and/or for a longer period than the first hydrolysis step. However, given that the second polysaccharide is also subjected to the first treatment stage, before removal of the hydrolysate resulting from the first polysaccharide, it may not always be necessary to subject the remaining second polysaccharide to an especially higher temperature and/or for longer and it may in fact be possible to achieve complete hydrolysis of the second polysaccharide at a lower temperature and/or for a shorter period that the first hydrolysis step.

In each of the first and second hydrolysis stages, the resulting hydrolysate is then separated from the solid materials, preferably through pressing of the treated material to separate the residue as a solid product. The solid product that is separated may be subjected to at least one wash cycle to remove any residual sugar solution from the solid. The wash cycle comprises washing the solid product with a suitable wash liquid. The wash liquid may be water. Normally the wash water is recycled water, for instance water that has been separated from the still bottoms liquor in the distillation recovery of the fermentation product in which suspended solids have been removed.

Since the wash water may contain other impurities which could be harmful to the fermentation process it would be desirable to minimise the amount of wash water used.

The liquid hydrolysate which contains sugars and acid can then be collected for further processing. When the first polysaccharide is hemicellulose, the resulting hydrolysate is generally $C_5$ sugars and when the second polysaccharide is cellulose the hydrolysate is generally $C_6$ sugars.

In each case it is important to adjust the pH of the acid sugar liquors to a pH of at least 4. The pH adjustment may be done by addition of a base or by use of an ion exchange resin, which is capable of neutralising the acid. Preferably the pH of the sugar liquor that results from the acid digestion process is adjusted to a pH of at least 10 to remove residual acid by addition of a base material such as sodium carbonate, and then afterwards by adjustment of the pH to a more neutral or slightly acidic pH. Desirably the pH may be adjusted to a value of between 10 and 12, preferably about 11, by addition of a base, followed by titrating to a pH 4 to 5, preferably about 4.5.

Alternatively, the acid may be removed from the liquor by passing the hydrolysate through a bed of resin beads to remove the acid. The aqueous sugar stream which desirably contains at least 98% of the sugar present in the hydrolysate can then be recovered.

The $C_5$ and $C_6$ sugars may be fed into the fermentation vessel as separate streams or alternatively they may be combined into a single stream which is delivered into the fermentation vessel.

After the separation of the acid from the sugar stream, the acid is preferably concentrated for reuse for example by evaporation.

The fermentation process of the present invention typically involves allowing the fermentation to proceed for 3 to 5 days. The fermentation product is separated from the broth by passing the broth comprising the fermentation product into a distillation stage, where the fermentation compound is collected as a distillate and the residue 'still bottoms' is removed. In one preferred aspect of the invention the fermentation product is separated from the broth by passing the broth comprising the fermentation product into a concentration stage, in which the fermentation compound is collected in the concentrate and extracted by at least one means selected from the group consisting of ion exchange, solvent extraction and electrodialysis.

The process can be used to prepare a range of fermentation products, but preferably the fermentation product is selected from the group consisting of ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid and tartaric acid and amino acids such as L-glutaric acid, L-lysine, L-aspartic acid, L-tryptophan, L-arylglycines or salts of any of these acids.

The microorganisms used in the fermentation process of the present invention can be, for example, a yeast such as *Klyveromyces* species, *Candida* species, *Pichia* species, *Brettanomyces* species, *Saccharomyces* species such as *Saccharomyces cerevisiae* and *Saccharomyces uvarum, Hansenula* species and *Pachysolen* species. Alternatively, the microorganism can be a bacterial species such as *Leuconostoc, Enterobacter, Klebsiella, Erwinia, Serratia, Lactobacillus, Lactococcus, Pediococcus, Clostridium, Acetobacter, Gluconobacter Lactobacillus, Aspergillus, Propionibacterium, Rhizopus* and *Zymomonas mobilis*. In addition genetically modified strains may also be used.

Since the solid product generally comprises lignin and analogous materials it can be particularly difficult to separate from the liquor. We have unexpectedly found that the production of fermentation product can be significantly improved by applying one or more flocculating agents to the separation of the hydrolysate from the solid product. We have found that the solid product can be more efficiently dewatered by the process and that a higher cake solids can be achieved. Since the solid product can be more efficiently dewatered there is a reduced requirement for separation equipment capacity and equipment that is less capital intensive and less expensive to operate, such as a filter press, can be used. Since higher cake solids can be achieved, less of the acid sugar solution remains in the residual by-product solid. Hence the quantity of water required to wash the by-product solid free of acid and sugar is much reduced, improving both the productivity and efficiency of the process.

Suitably the flocculating agent is selected from the group consisting of water-soluble or water-swellable natural, semi-natural and synthetic polymers and charged microparticulate materials. Preferably the polymer is synthetic and may be formed by polymerisation of at least one cationic, non-ionic or and/or anionic monomer(s) alone or with other water soluble monomers. By water soluble we mean that the monomer has a solubility of at least 5 g/100 ml at 25° C.

Preferably polymeric flocculating agents are formed from ethylenically unsaturated water soluble monomers that readily polymerise to produce high molecular weight polymers. Particularly preferred polymers include monomers that are selected from the group consisting of polyacrylic acid or polyacrylate salts, polyacrylamide, copolymers of acrylamide with (meth) acrylic acid or salts thereof, copolymers of acrylamide with dialkylaminoalkyl (meth) acrylate or acid addition or quaternary ammonium salts, polymers of diallyldimethyl ammonium chloride, polyamines and polyethylene imines. The polymers may be linear, branched or crosslinked.

The polymers may be prepared by any convenient conventional process, for instance by solution polymerisation, gel polymerisation, reverse phase suspension polymerisation and reverse phase emulsion polymerisation. Suitable processes include those described in EP-A-150933 or EP-A-102759.

Suitable polymers can be anionic, cationic or non-ionic polymers. The preferred polymers are non ionic or cationic polymers of sufficiently high molecular weight such that it exhibits an intrinsic viscosity of at least 4 dl/g. Such an intrinsic viscosity generally indicates a polymer of several million molecular weight, for instance generally greater than 5,000,000 and usually at least 7,000,000. In general the polymer preferably has an intrinsic viscosity greater than 6 dl/g, often at least 8 or 9 dl/g. The intrinsic viscosity can be as high as 30 dl/g or higher. In many cases though suitable cationic polymers exhibit an intrinsic viscosity in the range of 7 to 25 dl/g, in particular 10 to 20 dl/g, in particular around 14 or 15 dl/g.

Suitable cationic monomers include quaternary ammonium or acid salts of monomers which contain amine groups. Preferably the cationic polymer is formed from a monomer or blend of monomers comprising at least one cationic monomer selected from the group consisting of quaternary ammonium and acid salts of dimethylaminoethyl (meth) acrylate, quaternary ammonium and acid salts of dimethylaminoethyl (meth) acrylamide and diallyldimethyl ammonium chloride. The cationic monomers may be homopolymerised or copolymerised with other monomers, for instance acrylamide. The cationic polymers thus may be any polymer that carries a cationic charge, provided of course that they are of sufficiently high molecular weight to exhibit an intrinsic viscosity of at least 4 dl/g. Intrinsic viscosity is measured using a suspended level viscometer in 1 M NaCl buffered to pH 7.5 at 25° C.

The cationic polymers according to the invention may be prepared as substantially linear polymers or as branched or structured polymers. Structured or branched polymers are usually prepared by inclusion of polyethylenically unsaturated monomers, such as methylene-bis-acrylamide into the monomer mix, for instance as given in EP-B-202780. Preferably however, the polymers are substantially linear and are prepared in the form of a bead or powdered product.

Suitably the polymeric flocculating agent would be added as an aqueous solution or aqueous dispersion. The polymer may be added in an amount sufficient to effect flocculation. Typically the amount of polymeric flocculating agent sufficient to induce flocculation would be usually at least 0.002 weight % based on weight of suspended solids. Usually better flocculation and therefore separation can be achieved if at least 0.01% is used. The dose may be substantially higher, for instance up to 1%. However, optimum flocculation and separation is normally achieved using doses in the range of 0.015% to 0.2%, especially 0.02% to 0.1%. Following flocculation of the suspended solids the solid product can be separated from the hydrolysate aqueous liquor by mechanical means, for instance filter press, centrifuge, belt press, horizontal belt filter or pressure filter. The action of the flocculating agent greatly enhances the separation of the solids from the liquor by comparison to separation using solely mechanical means. We have found that the process of the present invention provides a higher cake solids, with less residual aqueous liquor, which means that a higher proportion of the sugar liquor is available for conversion into the fermentation product. Likewise we find that the aqueous liquor contains much lower levels of extraneous suspended cellulosic solids. Furthermore we also find that less wash water is required.

The solid product that results from the separation step should be as dry as possible in order to prevent any loss of sugar, which would otherwise be used in the fermentation process. In addition the solid by-product, which contains mainly lignin can be used as a solid fuel, for instance for use in the boiler used to heat the distillation column used in separating the fermentation product from the fermentation broth. Thus it is also important that when the solid lignin containing product is used as a fuel that it is as dry as possible.

In a further preferred embodiment of the present invention the flocculating agent is a charged microparticulate material. Particularly suitable examples of charged microparticulate materials include swellable clays, anionic, cationic or amphoteric microparticulate silica based materials and organic cross-linked polymeric microparticles.

The siliceous material may be any of the materials selected from the group consisting of silica based particles, silica microgels, colloidal silica, silica sols, silica gels, polysilicates, aluminosilicates, polyaluminosilicates, borosilicates, polyborosilicates, zeolites or swellable clay.

This siliceous material may be in the form of an anionic microparticulate material. Alternatively the siliceous material may be a cationic silica. Desirably the siliceous material may be selected from silicas and polysilicates.

The polysilicates of the invention may be prepared by reducing the pH of an aqueous solution of an alkali metal silicate. For instance polysilicic microgels otherwise known as active silica may be prepared by reducing the pH of an alkali metal silicate to between 2 and 10 by use of mineral acids or acid exchange resins, acid salts and acid gases. It may be desired to age the freshly formed polysilicic acid in order to allow sufficient three dimensional network structure to form. Generally the time of ageing is insufficient for the polysilicic acid to gel. Particularly preferred siliceous material include polyalumino-silicates. The polyaluminosilicates may be for instance aluminated polysilicic acid, made by first forming polysilicic acid microparticles and then post treating with aluminium salts. Alternatively the polyaluminosilicates may be polyparticulate polysicilic microgels of surface area in excess of 1000 m$^2$/g formed by reacting an alkali metal silicate with acid and water soluble aluminium salts. Typically the polyaluminosilicates may have a mole ratio of alumina:silica of between 1:10 and 1:1500.

Polyaluminosilicates may be formed by reducing the pH of an aqueous solution of alkali metal silicate to between 2 and 10 using concentrated sulphuric acid containing 0.2 to 2.0% by weight of a water soluble aluminium salt, for instance aluminium sulphate. The aqueous solution may be aged sufficiently for the three dimensional microgel to form. Typically the polyaluminosilicate is aged for up to about two and a half hours before diluting the aqueous polysilicate to 0.5 weight % of silica.

The siliceous material may be a colloidal borosilicate. The colloidal borosilicate may be prepared by contacting a dilute aqueous solution of an alkali metal silicate with a cation exchange resin to produce a silicic acid and then forming a heel by mixing together a dilute aqueous solution of an alkali metal borate with an alkali metal hydroxide to form an aqueous solution containing 0.01 to 30% $B_2O_3$, having a pH of from 7 to 10.5.

The swellable clays may for instance be typically a bentonite type clay. The preferred clays are swellable in water and include clays which are naturally water swellable or clays which can be modified, for instance by ion exchange to render them water swellable. Suitable water swellable clays include but are not limited to clays often referred to as hectorite, smectites, montmorillonites, nontronites, saponite, sauconite, hormites, attapulgites and sepiolites.

Most preferably the clay is a bentonite type clay. The bentonite may be provided as an alkali metal bentonite. Bentonites occur naturally either as alkaline bentonites, such as sodium bentonite or as the alkaline earth metal salt, usually the calcium or magnesium salt. Generally the alkaline earth metal bentonites are activated by treatment with sodium carbonate or sodium bicarbonate. Activated swellable bentonite clay is often supplied as dry powder. Alternatively the bentonite may be provided as a high solids flowable slurry, for example at least 15 or 20% solids.

When the charged microparticulate material comprises organic cross-linked polymeric microparticles. The microparticles may be made as microemulsions by a process employing an aqueous solution comprising a cationic or anionic monomer and crosslinking agent; an oil comprising a saturated hydrocarbon; and an effective amount of a surfactant sufficient to produce particles of less than about 0.75 micron in unswollen number average particle size diameter. Microbeads are also made as microgels by procedures described by Ying Huang et. al., Makromol. Chem. 186, 273-281 (1985) or may be obtained commercially as microlatices. The term "microparticle", as used herein, is meant to include all of these configurations, i.e. beads per se, microgels and microlatices.

The charged microparticle material may be used in amounts of at least 0.002% based on weight of suspended solids. Typically though the doses are usually as high as 0.8 or 1.0% or higher. When the charged microparticle material is inorganic, the dose is usually in excess of 0.06%, preferably in the range 0.1 to 0.6%. When the charged microparticle is organic the dose is typically below 0.3%, preferably in the range 0.02 to 0.1%.

Unexpectedly we have found that the hydrolysate liquor can be separated particularly rapidly when the flocculation is effected by employing a water-soluble or water-swellable polymer and a charged microparticulate material. In one aspect we find that particularly effective flocculation and separation of the solids from the liquor occurs when flocculation is effected by introducing an anionic microparticulate material into the mixture and then reflocculating by adding a cationic or substantially non-ionic polymer. In a further preferred embodiment of the present invention we find that especially fast and efficient separation of solids is achieved by a process in which flocculation is effected by introducing a cationic polymer into the mixture and then reflocculating by adding an anionic microparticulate material.

The following examples illustrate the invention.

EXAMPLE I 100 g of softwood chips ground to less than 2 mm were added to 400 g of water and heated to 190° C. Once at 190° C. sulphuric acid was added to a concentration of 0.7% under nitrogen pressure and the mixture was left for 3 minutes. The temperature was rapidly reduced to 80° C. and the insoluble solids present in the pre-hydrolysed slurry (containing 0.32% sulphuric acid) is then separated on a filter press. Solutions of flocculant or flocculants (at 0.2 to 0.5% solids) and/or microparticulate suspensions (at 0.5 to 15% solids) are added into the slurry with necessary agitation at a dose of 0.2 to 2 Kg per tonne of solids. The flocculants were found to increase the rate of free drainage by gravity through a porous belt, before preparation of a filter cake in a wedge zone and subsequent further dewatering in a pressure zone.

A method of removing the sugars remaining in the solid portion is to wash with (recycled) water.

The recovered solid portion is again prepared as a slurry with approximately 400 ml of water and heated to 215° C. Once at 215° C. sulphuric acid is added to a concentration of 0.4% under nitrogen and the mixture was left for 3 minutes. The temperature was rapidly reduced to 80° C. and the insoluble solids present in the pre-hydrolysed slurry (containing 0.32% sulphuric acid) is then separated on a filter press. Prior to pressing solutions of flocculent or flocculants (at 0.2 to 0.5% solids) and/or particulate suspensions (at 0.5 to 15% solids) are added into the slurry with necessary agitation at a dose of 0.2 to 2 Kg per tonne of solids. Flocculants increase the rate of free drainage by gravity through a porous belt, before preparation of a filter cake in a wedge zone and subsequent further dewatering in a pressure zone. The flocculated dewatered pressure belt filter cake containing predominantly lignin was further dewatered in a pressure filter to generate a cake with a high dry solids concentration (approximately 85% (w/w)) suitable for use as a fuel.

A method of removing the sugars remaining in the solid portion is to wash with (recycled) water.

After ion exchange to remove acetic acid, the liquid portion of the hydrolysate is acidified to pH 2 by the addition of sulphuric acid. Lime is then added to raise the pH to 10 and the hydrolysate is heated to 50° C. The pH of the liquid is then adjusted to the fermentation pH of 4.5 for 4 hours allowing gypsum crystals to form for separation by filtration.

Following the two-stage dilute acid hydrolysis the solid residues remaining can enter either the fermentation process or be separated for fuel.

EXAMPLE II

The efficiency separation of acid and sugar from the fermentation product of the invention was assessed using the equipment described herein and the results obtained will now be illustrated by way of example in the accompanying drawings in which:

FIGS. 6 and 7 are vertical sections through a device for separating liquid from the sample.

Figure 1:
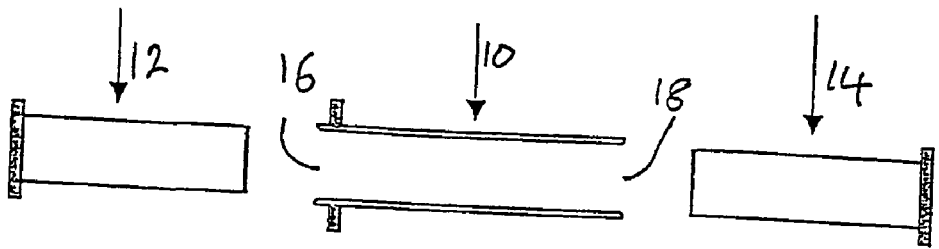
FIG. 1 is a diagrammatic axial section of a syringe.

Referring to FIG. 1 of the drawings an open ended syringe housing 10 of circular cross section is adapted to receive syringe plungers 12 and 14 into each open end 16 and 18 respectively.

Figure 2:
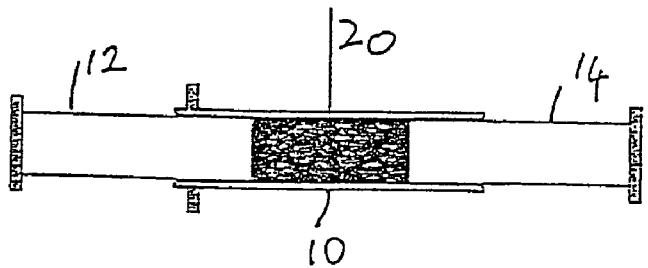
FIG. 2 shows the syringe of FIG. 1 containing a sample to be tested.
Figure 3:
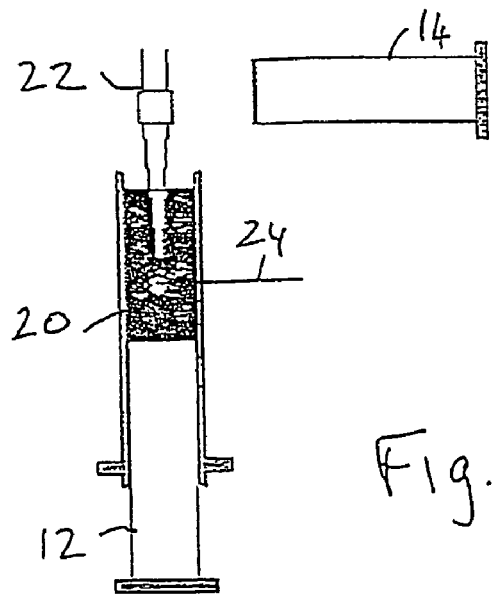
FIG. 3 illustrates the introduction of flocculant into the sample.

As shown in FIG. 2 a sample 20 of hydrolysate to be examined, optionally together with some ball bearings, is disposed in the syringe housing substantially in the mid part thereof and held in place by the plungers 12 and 14. The syringe together with the sample is incubated for a period of time, for example 15 minutes at a temperature that is typically about 90° C. After incubation one plunger is removed from the syringe and as shown in FIG. 3 polymer flocculent 24 is introduced into the sample with a pipette 22. The removed plunger is replaced and the syringe shaken in order to try to ensure that the polymer is distributed throughout the sample. The syringe is then incubated again for example for about ten minutes at a temperature of, for example, 90° C.

Figure 4:
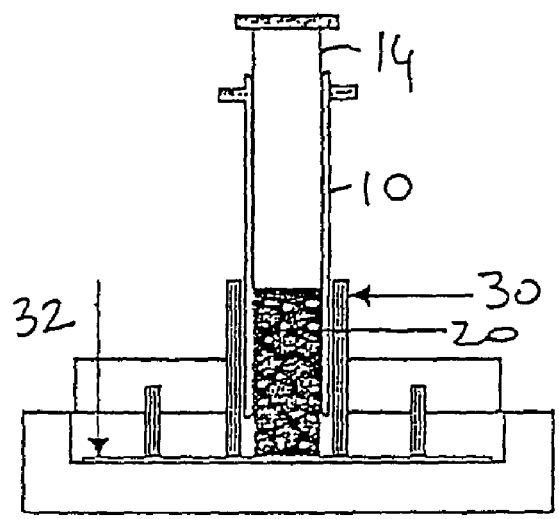
FIG. 4 shows a test rig in part sectional side elevation.
Figure 5:
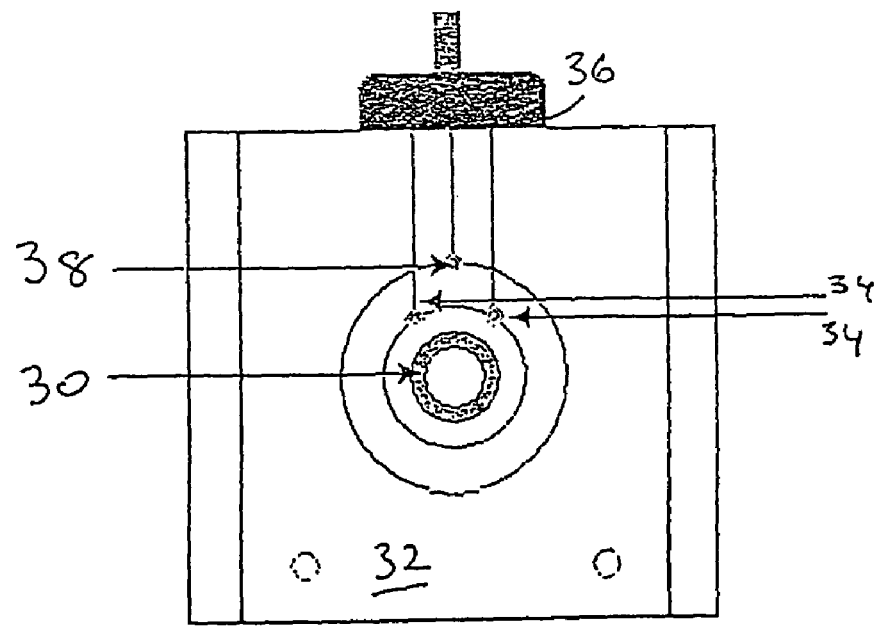
FIG. 5 is a part sectional plan view of the rig of FIG. 4.

The speed at which liquid separates from the solids in the sample can now be measured using the rig shown in FIGS. 4 and 5. This consists of a vertically oriented tube 30 sized to receive the syringe at its upper end. The lower end of tube 30 is disposed just above a filter paper 32. Contacts 34 are provided adjacent the filter paper which are arranged to supply a signal to a timer 36 to start the timer when liquid spreads to the contacts 34 from the tube. A further contact 38 linked to the timer is arranged to turn the timer off when liquid from the tube reaches contact 38. Thus the rig measures the time taken for liquid to spread across the filter paper from contact 34 to contact 38. This is known as Capillary Suction Time (CST) and is measure of the speed of separation of liquid from solids in the test sample.

To obtain the CST for the sample one plunger is removed and the syringe is inserted into the tube 30, the other plunger being moved into the syringe housing to bring the sample into contact with the filter paper 32 as illustrated in FIG. 4. Liquid separating from the sample spreads across the filter paper outwardly from the area of contact of the sample with the filter paper starting the timer when it reaches contacts 34 and stopping the timer when it reaches contact 38.

Using the above described equipment the CST was determined for 5 g. portions of hydrolysate with flocculant addition as shown in the following table:

The target CST was 98.8.

| Polymer Addition | CST seconds |
| --- | --- |
| Control + 100 μl H₂O | 127.9 |
| 100 μl of 1% Polymer 1 | 91.8 |

Polymer 1 is an acrylamide homopolymer with an IV of approx 15 dl/g.

EXAMPLE III

Following the procedure described with reference to FIGS. 1 to 3 after the second incubation at 80-90° C. one of the plungers is removed from the syringe and as shown in FIGS. 6 and 7 the open end of the syringe inserted into the open top of a larger syringe 40 having a perforated base 42 for supporting a mesh 44. A receiving cylinder 46 is positioned around the lower end of syringe 40 and the assembly of syringe 40 and cylinder 46 is mounted in flask 48 having a connection 50 to a vacuum. The sample is washed with water and the filtrate 52 collecting in the receiving cylinder can be examined.

The equipment with reference to FIGS. 6 and 7 was used to examine the separation of acid and sugar from a sample of hydrolysate treated in accordance with the invention.

Figure 8:
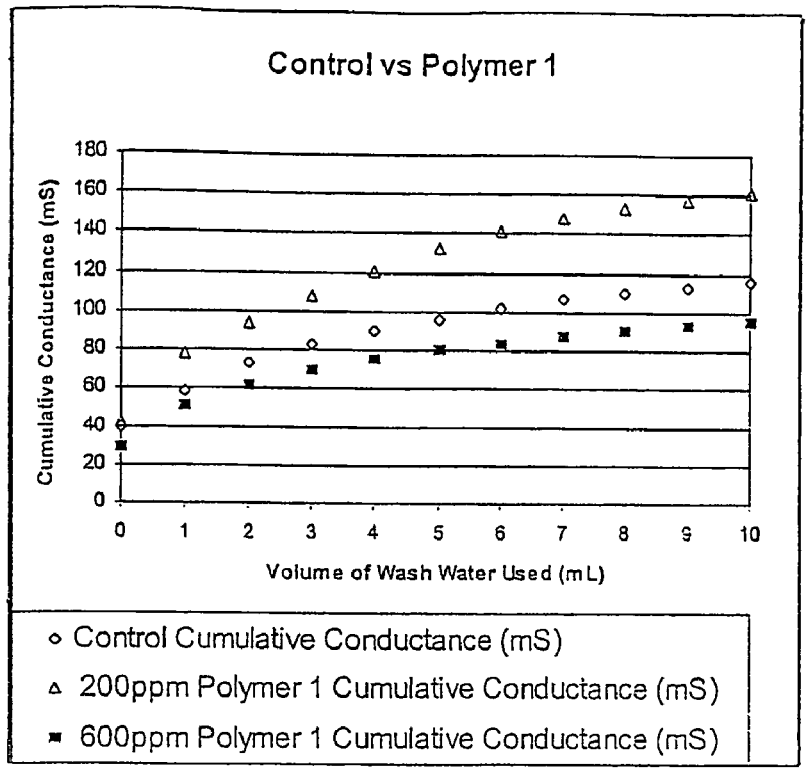
FIG. 8 is a graph showing the cumulative conductance, which arises from removal of the acid in the separated liquid

A 5 g sample of hydrolysate derived from corn stover was placed in the syringe housing 10 together with some ball bearings and held in place with the plungers during incubation. 200 ppm of Polymer 1 was introduced into the sample by a pipette as illustrated in FIG. 2. After the second incubation the sample and flocculant was transferred from syringe housing 10 to syringe 40, a 58 micron mesh having been provided on the perforated base 42. 10 ml of wash water was delivered to the syringe 40 while the vacuum was applied. The conductance of the filtrate was measured for each 1 ml of liquid recovered and the cumulative conductance results are shown on the graph of FIG. 8 which also shows the results obtained from a control sample. As can be seen the inclusion of the flocculant caused a rapid increase in the cumulative conductance on the addition of the wash water which indicates that acid is being removed with the wash water.

Figure 9:
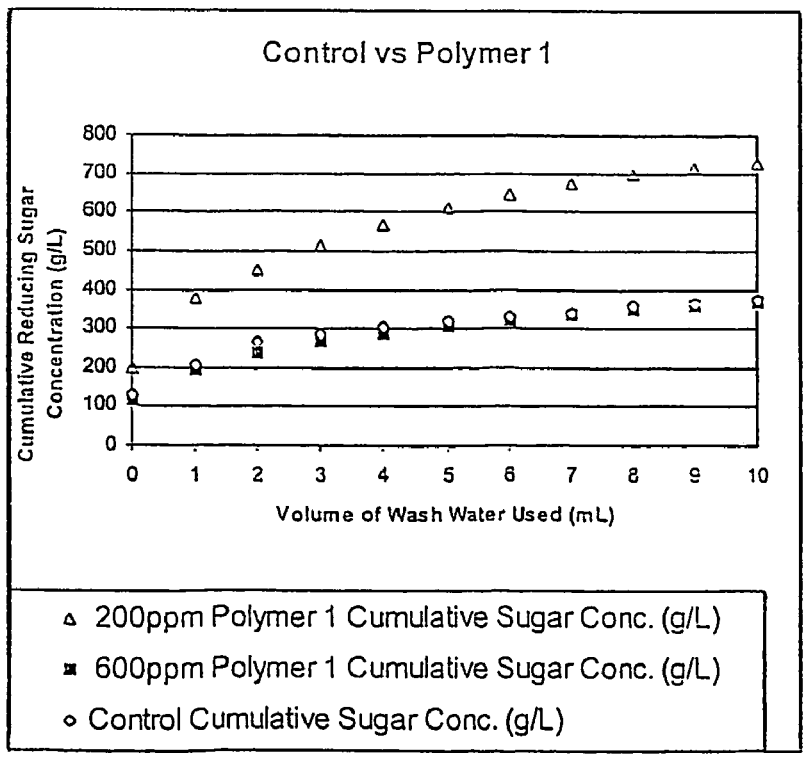
FIG. 9 is a graph of the cumulative amount of sugar removed in the separated liquid.

FIG. 9 shows the cumulative amount of sugar determined in the filtrate following the addition of wash water.

EXAMPLE IV

Following the same procedure as in Example II the actual amount of sugar recovered in the wash water was evaluated with two different polymers at two different polymer concentrations. The tests were performed twice at each concentration and the results are shown in the following Table 1.

| | Polymer Concentration | | | |
| --- | --- | --- | --- | --- |
| | 200 ppm | | 600 ppm | |
| Control | 190 mg | 181 mg | 249 mg | 237 mg |
| | 7.8 mls | 7.4 mls | 8.3 mls | 7.8 mls |
| Polymer 2 | 211 mg | 200 mg | 257 mg | 244 mg |
| | 7.4 mls | 7.0 mls | 8.1 mls | 7.7 mls |
| Polymer 1 | 386 mg | 367 mg | 246 mg | 233 mg |
| | 7.2 mls | 6.8 mls | 8.9 mls | 8.5 mls |

Polymer 2 is a copolymer or 8% sodium acrylate 92% acrylamide, IV approx 9 dl/g The above results are based on recovery of about 95% of the wash water. Recalculating the figures on the theoretical basis that all 10 mls of the wash water is recovered the results are as follows:

| | Polymer Concentration | | | |
| --- | --- | --- | --- | --- |
| | 200 ppm | | 600 ppm | |
| Control | 243 mg | 231 mg | 300 mg | 285 mg |
| Polymer 2 | 285 mg | 271 mg | 317 mg | 301 mg |
| Polymer 1 | 536 mg | 509 mg | 276 mg | 262 mg |

The invention claimed is:
1. A process of producing fermentation product comprising the steps of,
  (i) forming an acidified suspension of particulate plant derived material comprising a first polysaccharide which is more readily hydrolysable and a second polysaccharide which is more difficult to hydrolyse,
  (ii) allowing the first polysaccharide to undergo hydrolysis by action of the acid at a temperature of at least 50° C. under conditions such that the first polysaccharide is hydrolysed and thereby forming a mixture of an aqueous liquor containing dissolved sugar and a solid residue containing the second polysaccharide,

(iii) subjecting the acidic mixture to one or more separation stages in which the solid residue and aqueous sugar liquor are substantially separated from each other,
(iv) optionally washing the residue substantially free of the acid and the sugar,
(v) passing the solid cellulosic residue to a further treatment stage in which the residue is subjected to the action of dilute acid at a temperature of at least 50° C. under conditions such that the second polysaccharide is hydrolysed and thereby forming a mixture of an aqueous liquor containing dissolved sugar and a solid residue,
(vi) subjecting the acidic mixture to one or more separation stages in which the solid residue and aqueous sugar liquor are substantially separated from each other,
(vii) optionally washing the residue substantially free of the acid and the sugar,
(viii) adjusting the pH of the aqueous liquor from stages (iii), (iv), (vi) and (vii) to a pH of at least 4,
(ix) passing the aqueous liquor from stage (viii) to a fermentation stage where the dissolved sugars are acted upon by a microorganism in a fermentation broth to produce a fermentation product,
(x) separating the fermentation product from the broth, characterised in that the separation stage in steps (iii) and/or (vi) a flocculating agent is added to form a waste by-product, employing one or more flocculating agent(s) selected from the group consisting of water-soluble polymers, and water-swellable polymers and the water-soluble or water-swellable polymer is selected from the group consisting of polyacrylate salts, polyacrylamide, copolymers of acrylamide with (meth) acrylic acid or salts thereof, copolymers of acrylamide with dialkylaminoalkyl (meth)acrylate or acid addition or quaternary ammonium salts, polymers of diallyldimethyl ammonium chloride, polyamines and polyethylene imines,
the separation stage in steps (iii) and/or (vi) further includes mechanical means selected from the group consisting of a filter press, centrifuge, belt press, horizontal belt filter, and pressure filter, to separate the solid residue as cake solids.

2. A process according to claim 1 in which the plant derived material comprises materials selected from the group consisting of herbaceous biomass, softwood biomass, hardwood biomass, sewage sludge, paper mill sludge and the biomass fraction of municipal solid waste.

3. A process according to claim 1 in which the plant derived material is cellulosic and comprises hemicellulose as the first polysaccharide and cellulose as the second polysaccharide.

4. A process according to claim 1 in which the acid has a pKa of below 4 and has a concentration up to 2% by weight.

5. A process according to claim 1 in which the acid is selected from sulphuric acid and hydrochloric acid.

6. A process according to claim 1 in which the hydrolysis of the first polysaccharide is conducted at a temperature of between 120 to 220° C. for a period of from 1 minute to 15 minutes.

7. A process according to claim 1 in which the hydrolysis of the second polysaccharide is conducted at a temperature of between 120 to 220° C. for a period of from 1 minute to 15 minutes.

8. A process according to claim 1 in which the polymer is formed from a water-soluble monomer or blend of monomers.

9. A process according to claim 1 in which flocculation is effected by employing the water-soluble or water-swellable polymer and a charged microparticulate material.

10. A process according to claim 1 in which the solid residue comprises lignin.

11. A process according to claim 1 in which the fermentation product comprises a fermentation compound selected from the group consisting of ethanol, glycerol, acetone, n-butanol, butanediol, isopropanol, butyric acid, methane, citric acid, fumaric acid, lactic acid, propionic acid, succinic acid, itaconic acid, acetic acid, acetaldehyde, 3-hydroxypropionic acid, glyconic acid tartaric acid and amino acids wherein the amino acids are L-glutaric acid, L-lysine, L-aspartic acid, L-tryptophan, L-arylglycines or salts of any of these acids.

12. A process according to claim 11 in which the fermentation product is separated from the broth by passing the broth comprising the fermentation product into a distillation stage, where the fermentation compound is collected as a distillate and the residual still-bottoms is removed.

13. A process according to claim 11 in which the fermentation product is separated from the broth by passing the broth comprising the fermentation product into a concentration stage, in which the fermentation compound is collected in the concentrate and extracted by at least one means selected from the group consisting of ion exchange, solvent extraction and electrodialysis.

14. The process according to claim 1, wherein the flocculating agent is a flocculant that is formed from ethylenically unsaturated water soluble monomers selected from the group consisting of (meth) acrylic acid or salts thereof and acrylamide and the flocculant exhibits an intrinsic viscosity in the range of 7 to 25 dl/g.

* * * * *